(12) United States Patent
Jones et al.

(10) Patent No.: US 8,673,335 B2
(45) Date of Patent: Mar. 18, 2014

(54) METHODS AND COMPOSITIONS FOR SEALING AND ADHERING BIOLOGICAL TISSUES AND MEDICAL USES THEREOF

(75) Inventors: Curtis E. Jones, Savannah, GA (US); John P. Kennedy, Pooler, GA (US)

(73) Assignee: Southeastern Medical Technologies, LLC, Savannah, GA (US)

( * ) Notice: Subject to any disclaimer, the term of this patent is extended or adjusted under 35 U.S.C. 154(b) by 256 days.

(21) Appl. No.: 12/441,224

(22) PCT Filed: Sep. 13, 2007

(86) PCT No.: PCT/US2007/019846
§ 371 (c)(1), (2), (4) Date: Mar. 13, 2009

(87) PCT Pub. No.: WO2008/033417
PCT Pub. Date: Mar. 20, 2008

(65) Prior Publication Data
US 2010/0087851 A1    Apr. 8, 2010

Related U.S. Application Data

(60) Provisional application No. 60/844,234, filed on Sep. 13, 2006, provisional application No. 60/903,766, filed on Feb. 27, 2007.

(51) Int. Cl.
| | |
|---|---|
| *A61F 2/00* | (2006.01) |
| *A61F 13/00* | (2006.01) |
| *A61F 13/02* | (2006.01) |
| *A61K 9/70* | (2006.01) |
| *A61K 38/00* | (2006.01) |
| *A61K 35/14* | (2006.01) |
| *A61L 15/16* | (2006.01) |
| *A01N 37/18* | (2006.01) |
| *A61P 31/00* | (2006.01) |
| *C07C 209/00* | (2006.01) |
| *C07C 211/00* | (2006.01) |
| *C07K 14/00* | (2006.01) |
| *C07K 17/00* | (2006.01) |

(52) U.S. Cl.
USPC ........... 424/423; 424/425; 424/426; 424/443; 424/444; 424/445; 424/446; 424/448; 424/449; 514/1.1; 514/2.3; 530/380; 530/829; 530/836; 564/1; 564/3

(58) Field of Classification Search
USPC ......... 424/423, 425, 426, 443, 444, 445, 446, 424/448, 449; 514/1.1, 2.3; 530/380, 829, 530/836, 356, 362; 564/1, 3; 106/124, 106/124.4, 125; 602/50, 904
See application file for complete search history.

(56) References Cited

U.S. PATENT DOCUMENTS 2,816,099 A * 12/1957 Young et al. ................... 530/354
4,362,567 A    12/1982 Schwarz et al.

(Continued)

FOREIGN PATENT DOCUMENTS

| EP | 0629347 | 12/1994 |
|---|---|---|
| WO | 99/66964 | 12/1999 |

(Continued)

OTHER PUBLICATIONS http://en.wikipedia.org/wiki/Urea; reference dates beginning with 1956 to present; many reference resources undated; downloaded Dec. 7, 2011.*

(Continued)

*Primary Examiner* — Jane C Oswecki
(74) *Attorney, Agent, or Firm* — Nixon & Vanderhye PC

(57) ABSTRACT

Compositions and methods for sealing, coating and adhering tissues are provided that utilize a polymeric system comprising at least a Polymer and a crosslinking agent; and, optionally, (i) a Gelation Disrupting Agent, (ii) an Augmentative Polymer or Monomer, (iii) an Adjunct Compound (iv) an Antimicrobial Agent (v) an Adhesion Enhancer, (vi) a Crosslink Augmentating Agent or any combination thereof. Additionally, a Therapeutic Agent may be incorporated.

9 Claims, 4 Drawing Sheets

(56) References Cited

U.S. PATENT DOCUMENTS

Figure 3:
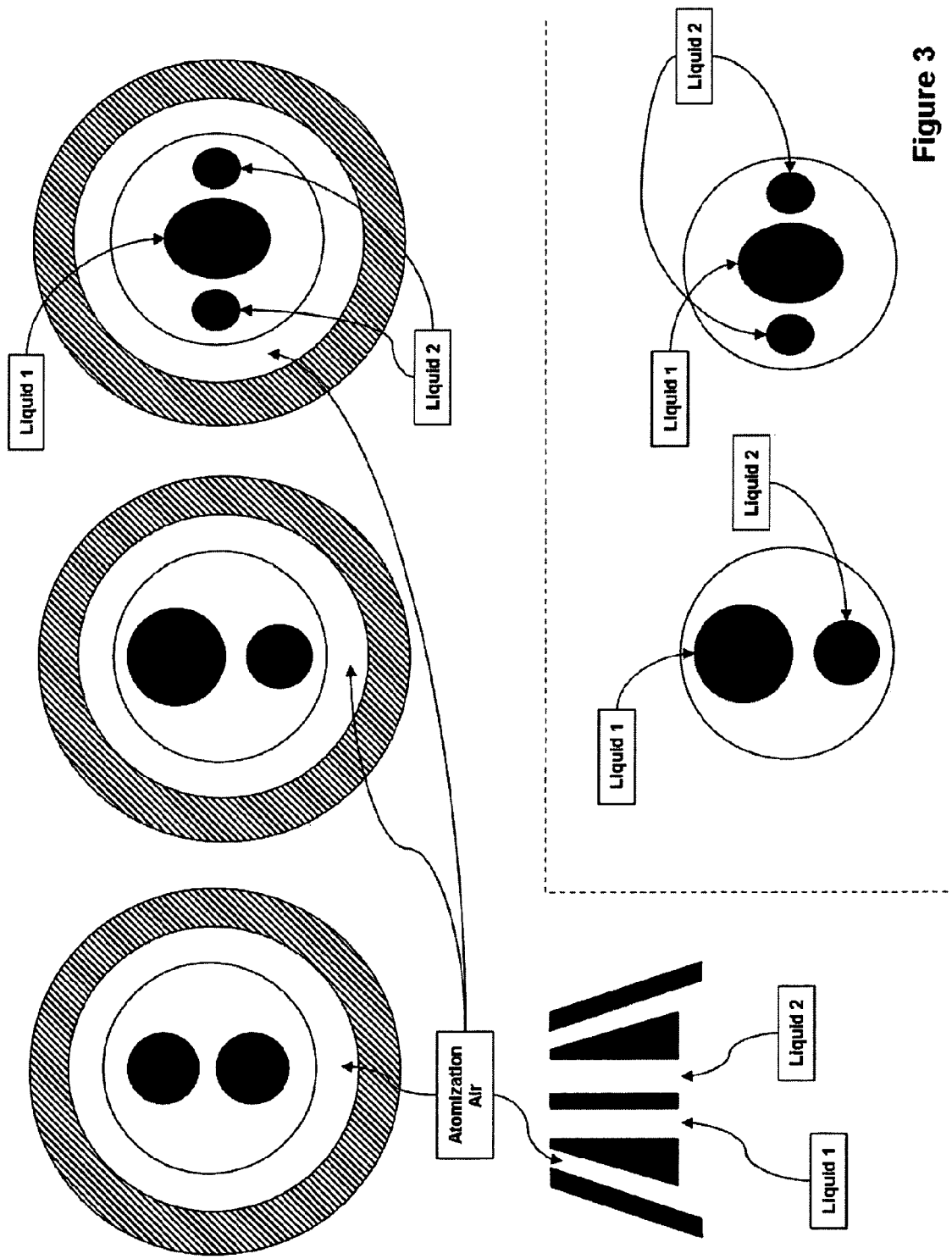

| | | | |
|---|---|---|---|
| 4,414,976 | A | 11/1983 | Schwarz et al. |
| 4,740,534 | A | 4/1988 | Matsuda et al. |
| 4,818,291 | A | 4/1989 | Iwatsuki |
| 5,213,580 | A | 5/1993 | Slepian et al. |
| 5,385,606 | A * | 1/1995 | Kowanko .................. 106/156.3 |
| 5,800,538 | A | 9/1998 | Slepian et al. |
| 6,372,229 | B1 | 4/2002 | Ollerenshaw et al. |
| 6,592,814 | B2 * | 7/2003 | Wilcox et al. ................... 422/28 |
| 7,799,767 | B2 * | 9/2010 | Lamberti et al. ................ 514/80 |
| 2002/0018802 | A1 * | 2/2002 | Meyer-Ingold et al. ...... 424/446 |
| 2005/0013842 | A1 | 1/2005 | Qiu et al. |
| 2005/0089539 | A1 | 4/2005 | Scholz et al. |
| 2007/0031467 | A1 | 2/2007 | Abrahams et al. |

FOREIGN PATENT DOCUMENTS

| | | |
|---|---|---|
| WO | 2004/024180 | 3/2004 |
| WO | 2006/083384 | 8/2006 |

OTHER PUBLICATIONS

Murray et al., "Gelling of Urea-Linked Gelatin with Fresh Frozen Plasma,"; May, 1989; Anaesthesia; 44(5): 392-393.*

Murray et al., "Gelling of Urea-Linked Gelatin with Fresh Frozen Plasma," May, 1989; Anaesthesia, 44(5):392-393.*

'Urea' Wikipedia [online], [retrieved Dec. 7, 2011] Retrieved from the Internet: <URL: http://en.wikipedia.org/wiki/Urea.*

Bachet, J. et al., "Four-Year Clinical Experience with the Gelatin-Resorcine-Formol Biological Glue in Acute Aortic Dissection", J. Thorac. Cardiovasc. Surg., vol. 83, 1982, pp. 212-215.

Bachet, J. et al., "Surgery of Type A Acute Aortic Dissection with Gelatine-Resorcine-Formol Biological Glue: A Twelve-Year Experience", J. Cardiovasc. Surg., vol. 31, Aug. 1990, pp. 263-273.

Basu, Samir et al., "Comparative Study of Biological Glues: Cryoprecipitate Glue, Two-Component Fibrin Sealant, and 'French Glue'", Ann. Thorac. Surg., vol. 60, 1995, pp. 1255-1262.

Bingley, John A. et al., "Late Complications of Tissue Glues in Aortic Surgery", Ann. Thorac. Surg., vol. 69, 2000, pp. 1764-1768.

Braunwald, Nina et al., "Evaluation of Crosslinked Gelatin as a Tissue Adhesive and Hemostatic Agent: An Experimental Study", Surgery, vol. 59, No. 6, Jun. 1966, pp. 1024-1030.

Eddy, A. Craig et al., "The Effects of Bioglue® Surgical Adhesive in the Surgical Repair of Aortic Dissection in Sheep", European Association for Cardio-Thoracic Surgery, Sep. 1998, 3 pgs.

Fabiani, Jean-Noël et al., "Use of Surgical Glue Without Replacement in the Treatment of Type A Aortic Dissection", Supplement I Circulation, vol. 80, No. 3, Sep. 1989, pp. 1-264-1-268.

Fukunaga, Suhji et al., "The Use of Gelatin-Resorcin-Formalin Glue in Acute Aortic Dissection Type A", European Journal of Cardio-Thoracic Surgery 15, 1999, pp. 564-570.

White, Jennifer K. et al., "The Use of a Novel Tissue Sealant as a Hemostatic Adjunct in Cardiac Surgery", The Heart Surgery Forum, vol. 3, Issue 1, 2000, pp. 56-61.

Supplementary EPO search report and opinion for corresponding European application, Serial No. 07811760.3, Laffargue-Haak, seven pages, mailed Oct. 17, 2011.

* cited by examiner

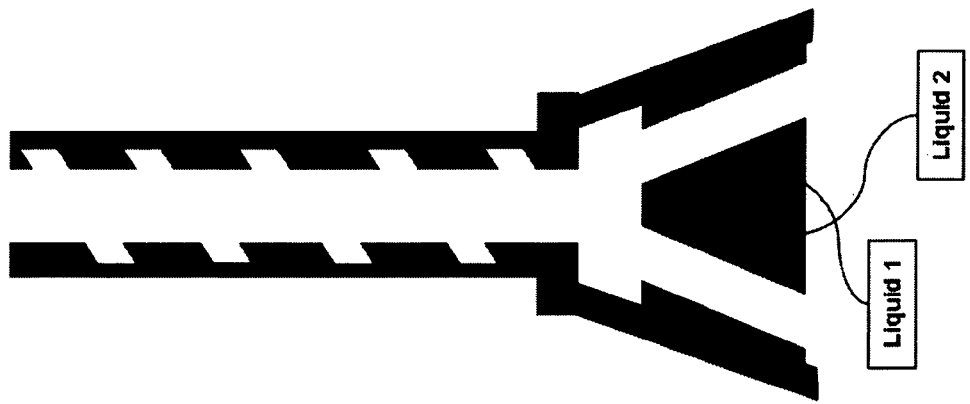
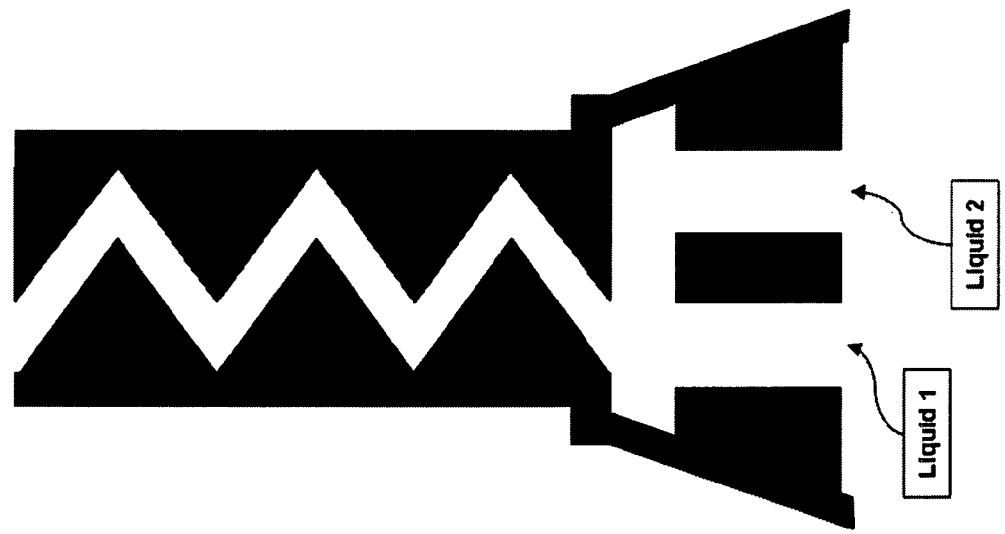
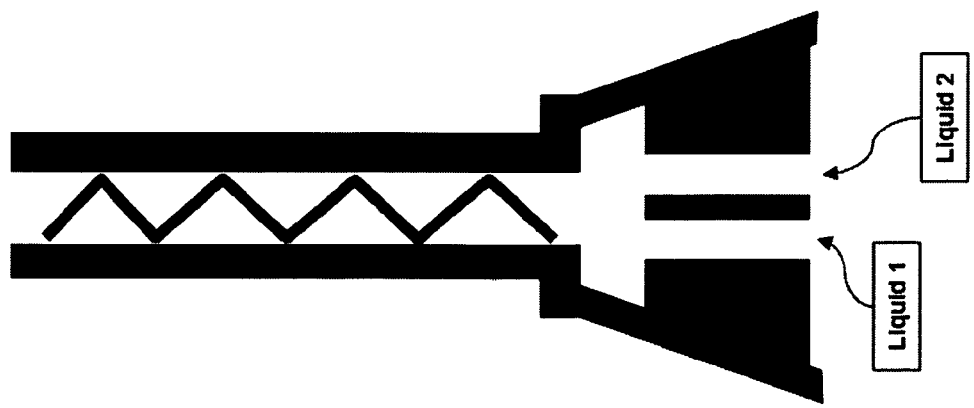
Figure 1

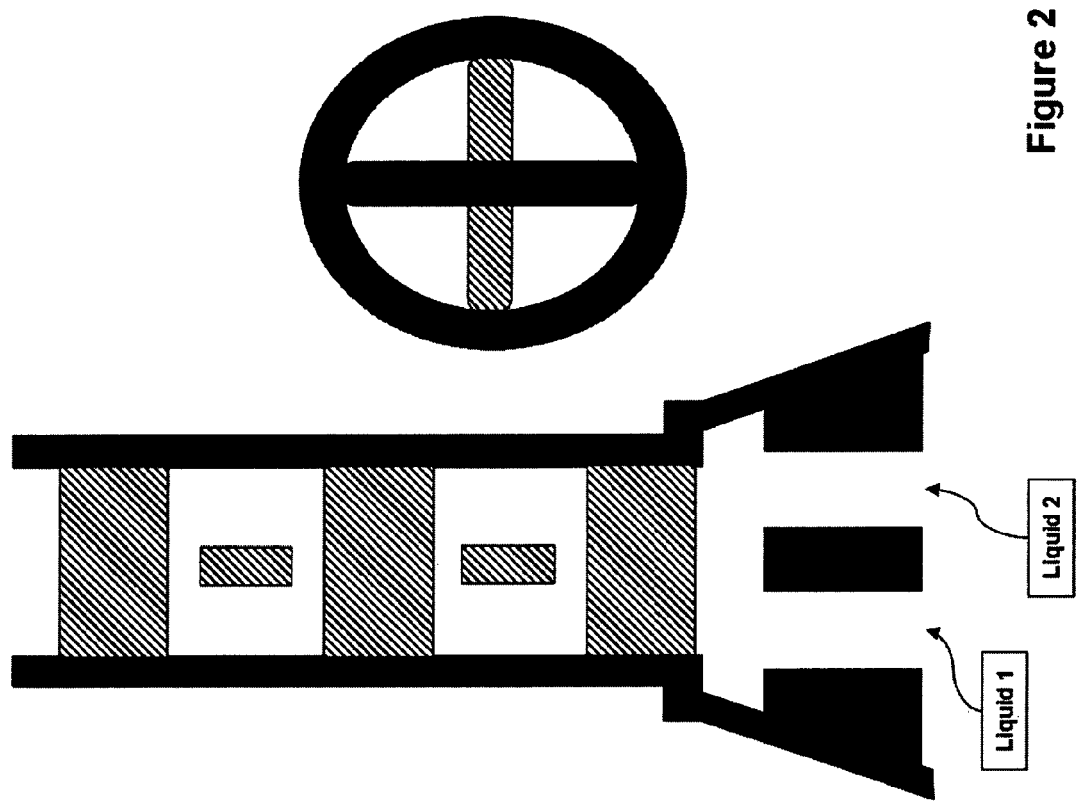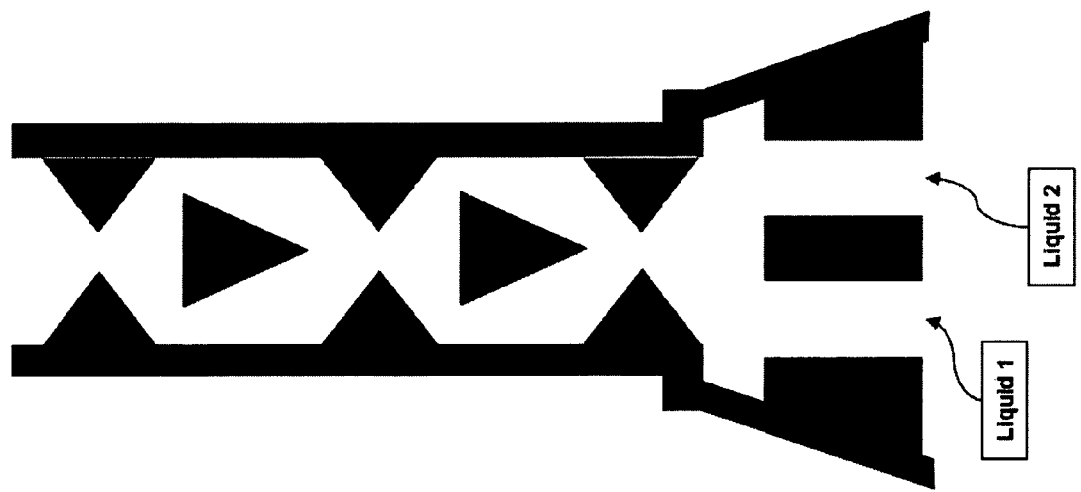
Figure 2

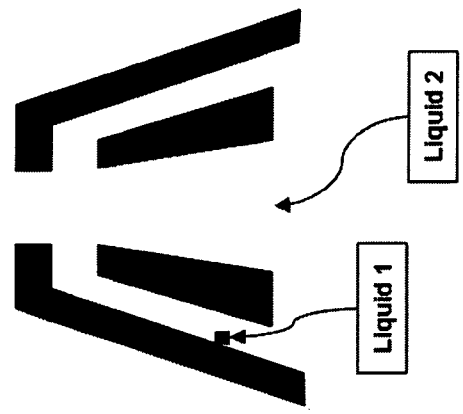
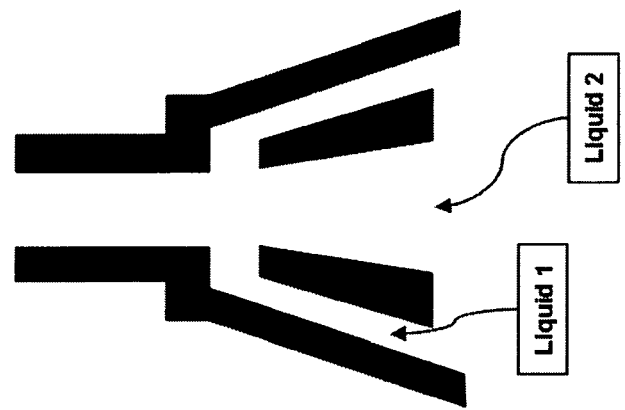
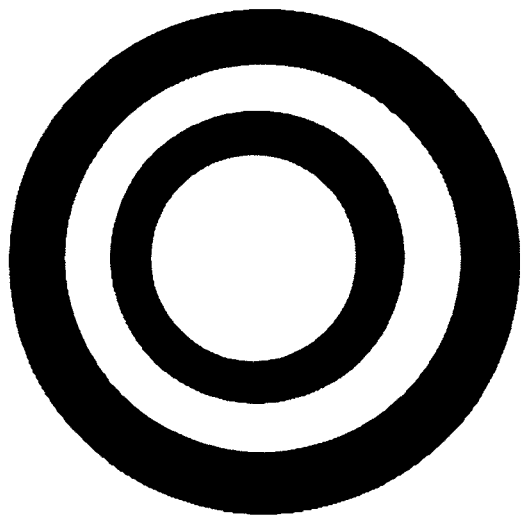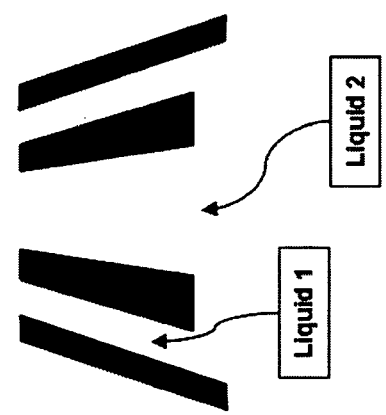
Figure 4

METHODS AND COMPOSITIONS FOR SEALING AND ADHERING BIOLOGICAL TISSUES AND MEDICAL USES THEREOF

This application is the U.S. national phase of International Application No. PCT/US2007/019846 filed Sep. 13, 2007 which designated the U.S. and claims priority to U.S. Provisional Patent Application Ser. No. 60/844,234 filed Sep. 13, 2006 and U.S. Provisional Patent Application Ser. No. 60/903,766 filed Feb. 27, 2007, the entire contents of each of which are hereby incorporated by reference.

BACKGROUND OF THE INVENTION

1. Field of the Invention

This invention relates to generally to sealants and adhesives, including the dressings and barriers that result from their use, for bio-medical applications. In particular, the invention relates to tissue sealants and adhesives used in Surgical, wound and trauma applications.

More specifically this invention discloses compositions and methods for Sealing or adhering tissues that are less toxic, less allergenic, less risk of infection, less risk of disease transmission by transmissible agents, more effective, less expensive and faster to biodegrade versus those of the prior art.

The need to repair damaged tissues is a common issue in medicine. The control of the loss of body fluids (i.e. bleeding, loss of CSF, etc.) and/or the ability to Seal and coat tissues following trauma, surgery or the progression of disease generally translates into decreased morbidity and mortality. Increased healing rates and decreased post operative complication rates are often additional great potential medical benefits. Historically, the use of sutures and biocompatible materials such as collagen, gelatin and oxidized cellulose has represented the standard of care. This approach relies on mechanical means (i.e. pressure), physical barriers, custom fitting and competent physiological processes to provide immediate success. In addition, the use of such biocompatible materials including Avitene®, Gelfoam®, and Surgicel® are often unreliable or even detrimental following closure of the tissue due to the propensity to migrate and the propensity of infection. The use of thrombin and fibrin glue products offer a greater degree of reliability, but the lack of mechanical strength, limited adhesion to moist tissues and the possibility of allergy limit their utility. Later advances in Surgical adhesives and sealants such as DuraSeal®, CoSeal® and BioGlue®, utilize cross-linked polymers, have increased the reliability of sealant and adhesive technology. However, the risk of allergy, the risk of BSE transmission, the toxicity at the tissue site, the lack of a convenient delivery device, extensive bio-resorption time, the low adhesive strength or reliance for specific applications, high swelling potential and the rates of infection associated with their use have proven problematic in varied degree for these new products when compared to traditional methods. In addition, in the case of the latter examples, acquisition costs represent a significant limiting factor in utilization. The present invention describes novel tissue sealant and adhesive methods and compositions that may be employed to design these products with improved mechanical strength and resilience, lower toxicity, lower swelling and lower infection rates. The invention may also be utilized to design sealants/adhesives that are more convenient, less variable in performance, less allergenic, less expensive, biodegrade in less time and possess less risk of disease by transmission by transmissible agents.

2. Related Art

A search of the prior art did not disclose any patents that read directly on the claims of the instant invention; however, the following references were considered related.

Journal: Braunwald et al. "Evaluation of crosslinked gelatin as a tissue adhesive and lenstatic agent: An experimental study". Surgery—June 1966, pp. 1024-1030.

Journal: Bachet et al.: "Four-year clinical experience with the gelatin-resorcine-formol biological glue in acute aortic dissection." J. Thorac. Cardioavasc. Surg. vol. 83 (1982), pp. 212-215.

Journal: Fabiani et al. "Use of Surgical Glue Without Replacement in the Treatment of Type A Aortic Dissection." Supplement I Circulation vol. 80, No. 3 (September 1989), pp. 1264-1268.

Journal: Bachet et al.: "Surgery of type A acute aortic dissection with Gelatine-Resorcine-Formol biological glue: A twelve-year experience." J. Cardiovasc. Surg. vol. 31 pp. 263-273 (August 1990).

Journal: Basu et al. "Comparative Study of Biological Glues: Cryoprecipitate Glue, Two-Component Fibrin Sealant, and "French" Glue". Ann Thorac Surg 1995; 60:1255-1262.

Journal: Eddy et al, "The Effects of Bioglue™ Surgical Adhesive in the Surgical Repair of Aortic Dissection in Sheep", European Association for Cardio-Thoracic Surgery, September 1998.

Journal: Suhji et al. "The use of gelatin-resorcin-formalin glue in acute aortic dissection type A". European Journal of Cardio-thoracic Surgery 15 (1999) 564-570.

Journal: White et al. "The Use of a Novel Tissue Sealant as a Hemostatic Adjunct in Cardiac Surgery". Heart Surgery Forum—March 2000, pp. 56-61.

Journal: Bingley et al. "Late Complications of Tissue Glues in Aortic Surgery". Ann Thorac Surg 2000; 69:1764-1768.

U.S. Pat. No. 4,362,567, inventors Schwarz et al, issued December 1982.

U.S. Pat. No. 4,414,976, inventors Schwarz et al, issued November 1983.

U.S. Pat. No. 4,740,534, inventor Takehisa, issued April 1988.

U.S. Pat. No. 4,818,291, inventor Iwatsuki, issued April 1989.

U.S. Pat. No. 5,385,606, inventor Kowanko, issued Jan. 1995.

U.S. Pat. No. 5,213,580, inventors Slepian et al, issued May 1993.

U.S. Pat. No. 5,800,538, inventors Slepian et al, issued September 1998.

U.S. Pat. No. 6,372,229, inventors Ollerenshaw et al, issued April 2002.

Consequently, a need has been demonstrated for the invention which provides compositions and methods which provide solutions to the problematic attributes described in the Background and Related Art.

SUMMARY OF THE INVENTION

The purpose of the invention is to provide solutions to the problems described in the Background, namely by teaching broad utility sealant, barrier and adhesive compositions and methods which provide improved mechanical strength and resilience, lower toxicity, lower swelling, lower infection rates, greater convenience and ease of use, less variability in performance, less allergic potential, less expense, faster biodegradation rates and less risk of disease by transmission by transmissible agents. A significant advantage of the invention is the broad utility can be adapted for. By way of examples only, the invention may be adapted to repair damaged tissue that is life threatening such as aortic repairs, nephritic trauma, vascular access sites, hepatic trauma and cardiovascular repairs. Alternatively, the invention may be adapted for employment for less critical procedures such as dural sealant repairs and sealants to prevent scar tissue via a barrier effect.

According to a first aspect of the invention, a composition and method are provided which, when applied by instruments, systems, and methods that embody the invention, seals, dresses, coats or adheres tissues.

In broad terms, a preferred embodiment of the invention is comprised of (a) a compound or composition selected from the group of a monomer, a polymer, derivatives of this group or any combination thereof; (b) a cross-linking agent; and (c) a modifier or any combination of modifiers.

One advantage of the invention is that modifiers are provided which improve at least one critical attribute of a sealant or adhesive including strength, resilience, toxicity, swelling, infection rates, ease of use, variability, allergic potential, degradation rate and the risk of disease by transmission. Another advantage of the invention is that, when desirable, it may be adapted to vary the strength, toxicity, swelling and degradation rate as optimal for specific applications.

According to another aspect of the invention, a composition and method are provided which, when applied by instruments, systems, and methods that embody the invention, seals, dresses, coats or adheres tissues.

In broad terms, a preferred embodiment of the invention is comprised of (a) an amino acid containing compound or composition selected from the group of proteins, peptides, poly amino acids, protein hydrolysates, peptide hydrolysates, derivatives of this group or any combination thereof; (b) a cross-linking agent; and (c) a modifier or any combination of modifiers.

One advantage of the invention is that modifiers are provided which improve at least one critical attribute of a sealant or adhesive including strength, resilience, toxicity, swelling, infection rates, ease of use, variability, allergic potential, degradation rate and the risk of disease by transmission. Another advantage of the invention is that, when desirable, it may be adapted to vary the strength, toxicity, swelling and degradation rate as optimal for specific applications.

In broad terms, a preferred embodiment of the invention is comprised of (a) an amino acid containing compound or composition selected from the group of lactoferrin, lactoferrin peptides, lactoferrin hydrolysates, derivatives of this group or any combination thereof; and (b) a cross-linking agent; and optionally, (c) a modifier or any combination of modifiers.

One advantage of the invention is that improvements to the critical attributes of a sealant or adhesive are realized by the utilization of lactoferrin derivatives without the requirement of modifiers to achieve such improvements. Another advantage of the invention is that modifiers are provided which improve at least one critical attribute of a sealant or adhesive even further than the lactoferrin derivative alone including strength, resilience, toxicity, swelling, infection rates, ease of use, variability, allergic potential, degradation rate and the risk of disease by transmission. Another advantage of the invention is that, when desirable, it may be adapted to vary the strength, toxicity, swelling and degradation rate as optimal for specific applications. Another advantage of the invention is that lactoferrin derivatives do not have the viral transmission risk associated with bovine albumin and bovine gelatin.

One advantage of the invention is that improvements to the critical attributes of a sealant or adhesive are realized by the utilization of lactoferrin derivatives without the requirement of Modifiers to achieve such improvements. Another advantage of the invention is that Modifiers are provided which improve at least one critical attribute of a sealant or adhesive even further than the lactoferrin derivative alone including strength, resilience, toxicity, swelling, infection rates, ease of use, variability, allergic potential, degradation rate and the risk of disease by transmission. Another advantage of the invention is that, when desirable, it may be adapted to vary the strength, toxicity, swelling and degradation rate as optimal for specific applications. Another advantage of the invention is that lactoferrin derivatives do not have the viral transmission risk associated with bovine albumin and bovine gelatin.

According to another aspect of the invention, methods are provided which, when applied to the manufacturing of sealants and adhesive disclosed herein improve efficiency, output and the stability/performance of the products.

In broad terms, a preferred embodiment of the invention is comprised of (a) preparing at least one component by heating to a temperature of 35-150 degrees C.; and (b) completing this preparation stage with a regimen selected from the group of (i) allowing the composition to return to ambient temperature, (ii) cooling to about 4-10 degrees C. before returning to ambient temperature, (iii) allowing the composition to return to ambient temperature, and then adding additional components if utilized excluding the crosslinking agent, (iv) adding additional components if utilized excluding the crosslinking agent while above ambient temperature, or (v) cooling to about 4-10 degrees C. before returning to ambient temperature, and then adding any additional components if utilized excluding the crosslinking agent.

One advantage of the invention is improvements to production efficiency. Another advantage of the invention is improvements to product output. Another advantage of the invention is improvements to product stability and performance.

According to another aspect of the invention, methods are provided which, when applied to the delivery of sealants and adhesive disclosed herein improve ease of use and performance of the products.

In broad terms, a preferred embodiment of the invention is comprised initially a multiple part system comprising: [1] providing one part at least composed of component (a); [2] providing at least another part composed of component (b); and [3] completing the delivery with a regimen selected from the group of (i) mixing the separate parts by mechanical or fluid means prior to application, (ii) mixing the separate parts by mechanical or fluid means during application, or (iii) applying one part to the treatment site and subsequently any remaining parts to the desired treatment site to form a seal, a coating or an adhesion within or between tissues of the body.

One advantage of the invention is that the regimens of ordered combination and delivery improve the ease of use during application. Another advantage of the invention is that by controlling the ordered combination and delivery improvements in performance and variability are realized.

According to another aspect of the invention, methods are provided which, when applied to the delivery of sealants and adhesive disclosed herein improve ease of use and performance of the products.

In broad terms, a preferred embodiment of the invention is comprised initially a multiple part system comprising: [1] providing one part is at least composed of component (a); [2] providing at least another part composed of component (b); and [3] completing the delivery with a regimen selected from the group of (i) mixing the parts to create a final mixture and atomizing the final mixture in less than 2 minutes, or (ii) atomizing the separate parts together creating a final mixture via atomization.

One advantage of the invention is that the regimens of ordered combination and delivery improve the ease of use for specific applications that prefer spray delivery. Another advantage of the invention is that by controlling the ordered combination and delivery improvements in performance and variability are realized when rapid and broadcast delivery is preferred.

According to another aspect of the invention, methods are provided which, when applied to the delivery of sealants and adhesive disclosed herein improve ease of use and performance of the products.

In broad terms, a preferred embodiment of the invention is comprised of utilizing a mixing tip in single phase or alternating phase configuration selected from the group of (i) an auger; (ii) a zigzag; (iii) a baffle or (iv) a swirl to mix the parts just prior to contact with the site of application.

One advantage of the invention is that the configurations of mixing tips improve the ease of use for applications that prefer specific point of use delivery. Another advantage of the invention is that by controlling mixing and delivery improvements in performance and variability are realized.

According to another aspect of the invention, methods are provided which, when applied to the delivery of sealants and adhesive disclosed herein improve ease of use and performance of the products.

In broad terms, a preferred embodiment of the invention is comprised of utilizing a spray tip in a configuration selected from the group of (i) a dual liquid feed, and optionally a dual port, with air atomization; (ii) a dual liquid feed with hydraulic atomization; or (iii) a coaxial liquid feed, and optionally a dual port, with air or hydraulic atomization to combine the components during application to desired site.

One advantage of the invention is that the configurations of spray tips improve the ease of use for specific applications that prefer spray delivery. Another advantage of the invention is that by controlling the ordered combination and delivery improvements in performance and variability are realized when rapid and broadcast delivery is preferred.

According to another aspect of the invention, a composition and method are provided which, when applied by instruments, systems, and methods that embody the invention, seals, dresses, coats or adheres tissues.

In broad terms, a preferred embodiment of the invention is comprised of adding to the sealant and adhesive compositions disclosed herein, an effective amount of visible application indicator useful to aid and verify application to a desired site including a dye, a pigment, a fluorescent compounds, a radiolabeled compound, methylene blue, gentian violet, derivatives of this group, or any combination thereof.

One advantage of the invention is that the indicator allows the clinician to rapidly determine where the product has been applied. Another advantage of the invention is that the indicator provides rapid estimation of coating thickness during application.

According to another aspect of the invention, a composition is provided which, when applied by instruments, systems, and methods that embody the invention, seals, dresses, coats or adheres tissues.

In broad terms, a preferred embodiment of the invention is comprised of adding to the sealant and adhesive compositions disclosed herein, an effective amount of a therapeutic agent or combinations thereof.

One advantage of the invention is that therapeutic agents may augment or inhibit coagulation at the site depending on the risk of blood loss or embolism. Another advantage of the invention is that therapeutic agents may be selected to potentiate healing of the tissue at the site.

Further aspects of the invention will become apparent from consideration of the drawings and the ensuing description of preferred embodiments of the invention. A person skilled in the art will realize that other embodiments of the invention are possible and that the details of the invention can be modified in a number of respects, all without departing from the inventive concept. Thus, the following drawings and description are to be regarded as illustrative in nature and not restrictive.

BRIEF DESCRIPTION OF THE SEVERAL VIEWS OF THE DRAWINGS

FIG. 1 shows an auger, zigzag and swirl mixing tip.

FIG. 2 shows baffle mixing tip designs.

FIG. 3 shows air atomization and hydraulic atomization designs for two part systems.

FIG. 4 shows coaxial tip designs.

DESCRIPTION OF SPECIFIC EMBODIMENTS OF THE INVENTION

Definitions

As used in this description and the accompanying claims, the following terms shall have the meanings indicated, unless the context otherwise requires:

"Polymer" as used herein, means broadly any compound, natural or synthetic, made up of chemically linked subunits including, but not limited to, homopolymers, copolymers, proteins, peptides, glycosides including compounds with glycosidic bonds, nucleic acids and carbohydrates.

"Monomer" as used herein, means broadly any compound, natural or synthetic, that is a primary subunit of a polymer including simple sugars, amino acids, and nucleotides.

"Modifier" as used herein, is a compound added to the referenced composition to alter the properties of the composition. As used herein a modifier may be selected from the group of a gelation disruptor, an augmentative polymer or monomer, an adjunct compound, an adhesion enhancer, a crosslink augmentating agent, or an antimicrobial agent.

- "gelation disruptor or gelation disrupting agent" as used herein, means broadly any compound that functions to disrupt gelation including inhibiting gelation, altering the transition point or temperature or lowering the viscosity of polymeric systems which gel.
- "adjunct compound" as used herein, means broadly any compound which is a secondary component added to support the primary functional components. When used in a formulation these adjunct compounds may be useful for altering the mechanical properties of the product before or after dispensing.
- "augmentative polymer or monomer" as used herein, means broadly any polymer or onomer composed of reactive or interactive elements or groups. When used in a formulation, these polymers or monomers may contribute to the mechanical properties of the product before or after dispensing.
- "adhesion enhancer" as used herein, means broadly any compound which alters the adhesive strength, adhesive resilience or work required to overcome adherence, of a composition for a substrate.

"crosslink augmentating agent" as used herein, means broadly any compound which chemically or physically augments the crosslinks of a composition thereby enhancing the mechanical properties of a composition.

"antimicrobial agent or antimicrobial" as used herein, means broadly any compound with anti-infective attributes. This definition is expressly not limited to compounds classified as antibiotics.

"Therapeutic Agent" and "Therapeutic" when used herein means having or exhibiting the ability to heal, treat or provide other benefits, including a substance or composition having or exhibiting the ability to heal, treat or generally provide a benefit.

"Mechanical Properties" as used herein, mean broadly the physical or mechanical properties of the referenced compound or composition that can be measured or perceived.

"Controlling Biological Fluids" as used herein, means broadly the modulation of biological fluid equilibrium and flow as it relates to the biological site reference. Such modulation includes at least the partial limitation of fluid loss, the maintenance of critical fluids and the preservation of fluid physiological balance where gradients are relevant.

"Biological Fluids" as used herein, means broadly any fluid contained within or excreted from a human or animal including blood, urine, saliva, serous fluid, synovial fluid, gastric secretions, cerebrospinal fluid, sweat, tears, bile, chyme, mucous, vitreous humor, lymph, wound exudate or combinations thereof.

"Surgical" as broadly used herein includes any tissue invasive or disruptive procedure such as cutting, abrading, suturing, laser or otherwise physically changing body tissues regardless of the profession of any individual performing such procedures. For example, surgical as defined herein includes dental extractions by dentists and vascular interventions by interventional radiologist.

"Seal or sealing tissues" as used herein, means broadly to apply a composition to any tissue for the purpose of forming a seal, protective barrier, functional coating or primary dressing. When used in medical practice, the seals, barriers, coatings or dressings formed have a multiple of applications including prevention of scar tissue, controlling biological fluids, augmenting hemostasis and preventing contamination by foreign or unwanted biological compounds, tissues, organisms or compositions.

The present invention has utility in applications where prior art sealants and adhesives were previously used to bond tissues, to form protective seals or to form protective barriers. The invention is competent in sealing tissues alone or in combination with traditional closure methods such as sutures. The composition may be applied by a multiplicity of methods as dictated by the given indication, procedure or technique.

The system is readily formed by combining separate parts, two being the simplest, at the point of use as a broader application or spray. The first part comprises a solution, suspension or emulsion containing at least a polymer containing reactive sites. Alternatively, the first part may additionally contain modifiers or any combination of modifiers. The second part contains a solution, suspension or emulsion containing at least a cross-linking agent. Alternatively, the second part may additionally contain modifiers or any combination of modifiers if chemically stable. The parts may be combined just prior to application or during application in a number of different methodologies as described below. The systems may be provided in kits with independent syringes that may be combined by fluid mixing between the syringes at a union tip adapted for mixing and point delivery or spray delivery. In addition, the parts can be combined in vivo. The polymer containing part may be applied to the relevant tissues followed by application of the cross-linking agent containing part, or vise versa. The preferred application method may be customized to and driven by the requirements of indication, procedure or technique.

I. Compositions & Methods Dependent on Polymers

Broadly preferred compositions and methods are disclosed which significantly improve at least one critical attribute of a sealant or adhesive including strength, resilience, toxicity, swelling, infection rates, ease of use, variability, allergic potential, degradation rate and the risk of disease by transmission. The compositions and methods utilize multiple parts initially which are combined just prior to or during applications via several delivery methodologies.

A first best mode of the invention involves the utility of a monomer, a polymer, derivatives of this group or any combination thereof, a crosslinking agent and at least one modifier, which can significantly improve the critical attributes.

In second best mode, the polymer of the first best mode is an amino acid containing compound selected from the group of proteins, peptides, poly amino acids, protein hydrolysates, peptide hydrolysates, derivatives of this group or any combination thereof.

In third best mode, the composition of the first best mode further comprises an effective amount of visible application indicator useful to aid and verify application to a desired site including a dye, a pigment, a fluorescent compounds, a radio-labeled compound, methylene blue, gentian violet, derivatives of this group, or any combination thereof.

In fourth best mode, the composition of the first best mode further comprises an effective amount of a therapeutic agent including tissue growth promoters, blood products, thrombin, fibrinogen or combinations thereof.

One method of the invention may be operated by administering by positive pressure an effective amount of a formulation comprising: (a) a monomer, a polymer, derivatives of this group or any combination thereof; (b) a cross-linking agent; and (c) a modifier or any combination of modifiers, at the site for a period of time effective to seal, coat or adhere the tissue at the site. Another method of the invention may be operated by administering by positive pressure an effective amount of a formulation comprising: (a) an amino acid containing compound or composition; (b) a cross-linking agent; and (c) a modifier or any combination of modifiers, at the site for a period of time effective to seal, coat or adhere the tissue at the site. Another method of the invention may be operated by incorporating an effective amount of a direct or indirect visible indicator including a dye, a pigment, a fluorescent compounds, a radio-labeled compound, methylene blue, gentian violet, derivatives of this group, or any combination thereof, within the composition of the first method at a concentration effective to visually aid application at the site.

Another preferred embodiment disclosed broadly comprises an amino acid derivative, a cross-linking agent and a gelation disrupting agent. A best mode of the invention employs proteins, such as gelatin, albumin or lactoferrin, combined with glutaraldehyde and urea. A second best mode of the invention also includes a polymer containing a functional element such as chitosan, a crosslink augmentating agent such as vanillin, an adhesion enhancer such as dextran, an antimicrobial agent such as sodium laurate or any combination thereof.

Another preferred embodiment disclosed broadly comprises an amino acid derivative, a cross-linking agent and an antimicrobial agent. A best mode of the invention employs proteins, such as gelatin, albumin or lactoferrin, combined with glutaraldehyde and urea. A second best mode of the invention also includes sodium laurate. Another best mode of the invention also includes a polymer containing a functional element such as chitosan, a crosslink augmentating agent such as vanillin, an adhesion enhancer such as dextran and any combination thereof.

Another preferred embodiment disclosed broadly comprises an amino acid derivative, a cross-linking agent and an adhesion enhancer. A best mode of the invention employs proteins, such as gelatin, albumin or lactoferrin, combined with glutaraldehyde and dextran. A second best mode of the invention also includes a polymer containing a functional element such as chitosan, a crosslink augmentating agent such as vanillin, a gelation disruption agent such as urea, an antimicrobial agent such as sodium laurate and any combination thereof.

Another preferred embodiment disclosed broadly comprises an amino acid derivative, a cross-linking agent and a polymer containing a functional element. A best mode of the invention employs proteins, such as gelatin, albumin or lactoferrin, combined with glutaraldehyde and chitosan. A second best mode of the invention also includes a gelation disruption agent such as urea, a crosslink augmentating agent such as vanillin, an adhesion enhancer such as dextran, an antimicrobial agent such as sodium laurate and any combination thereof.

Another preferred embodiment disclosed broadly comprises an amino acid derivative, a cross-linking agent and a crosslink augmentating agent. A best mode of the invention employs proteins, such as gelatin, albumin or lactoferrin, combined with glutaraldehyde and vanillin. A second best mode of the invention also includes a polymer containing a functional element such as chitosan, a gelation disruption agent such as urea, an adhesion enhancer such as dextran, an antimicrobial agent such as sodium laurate and any combination thereof.

A preferred embodiment of the invention contains approximately gelatin 35% and urea 35% in the first part with the balance consisting of water or a physiologically compatible buffer. A more preferred embodiment of the invention contains approximately gelatin 25% and urea 25% in the first part with the balance consisting of water or a physiologically compatible buffer. A most preferred embodiment of the invention contains approximately gelatin 20% and urea 20% in the first part with the balance consisting of water or a physiologically compatible buffer. A most preferred embodiment of the invention contains approximately gelatin 17.5% and urea 17.5% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately gelatin 35%, urea 35% and chitosan in the range of 0.001%-5% in the first part with the balance consisting of water or a physiologically compatible buffer. A more preferred embodiment of the invention contains approximately gelatin 25%, urea 25% and chitosan in the range of 0.005%-5% in the first part with the balance consisting of water or a physiologically compatible buffer. A most preferred embodiment of the invention contains approximately gelatin 20%, urea 20% and chitosan in the range of 0.075%-2% in the first part with the balance consisting of water or a physiologically compatible buffer. A most preferred embodiment of the invention contains approximately gelatin 17.5%, urea 17.5% and chitosan in the range of 0.1%-0.5% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately gelatin 35%, urea 35% and chitosan in the range of 0.001%-5% alternatively with vanillin 0.001%-5% in the first part with the balance consisting of water or a physiologically compatible buffer. A more preferred embodiment of the invention contains approximately gelatin 25%, urea 25% and chitosan in the range of 0.005%-3% alternatively with vanillin 0.01%-4% in the first part with the balance consisting of water or a physiologically compatible buffer. A most preferred embodiment of the invention contains approximately gelatin 20%, urea 20% and chitosan in the range of 0.075%-1% alternatively with vanillin 0.1%-3% in the first part with the balance consisting of water or a physiologically compatible buffer. A most preferred embodiment of the invention contains approximately gelatin 17.5%, urea 17.5% and chitosan in the range of 0.1%-0.5% alternatively with vanillin 0.5%-3% in the first part with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately gelatin 35%, urea 35% and chitosan in the range of 0.001%-5% and dextran (mw 40,000-150,000 da) in the range of 0.001%-5% in the first part with the balance consisting of water or a physiologically compatible buffer. A more preferred embodiment of the invention contains approximately gelatin 25%, urea 25% and chitosan in the range of 0.005%-3% and dextran (mw 40,000-150,000 da) in the range of 0.05%-4% in the first part with the balance consisting of water or a physiologically compatible buffer. A most preferred embodiment of the invention contains approximately gelatin 20%, urea 20% and chitosan in the range of 0.075%-2% and dextran (mw 40,000-150,000 da) in the range of 0.5%-3% in the first part with the balance consisting of water or a physiologically compatible buffer. A most preferred embodiment of the invention contains approximately gelatin 17.5%, urea 17.5% and chitosan in the range of 0.1%-0.5% and dextran (mw 40,000-150,000 da) in the range of 0.5%-3% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately gelatin 35%, urea 35% and chitosan in the range of 0.001%-5% and glucosamine in the range of 0.001%-15% in the first part with the balance consisting of water or a physiologically compatible buffer. A more preferred embodiment of the invention contains approximately gelatin 25%, urea 25% and chitosan in the range of 0.005%-3% and glucosamine in the range of 0.05%-12% in the first part with the balance consisting of water or a physiologically compatible buffer. A most preferred embodiment of the invention contains approximately gelatin 20%, urea 20% and chitosan in the range of 0.075%-2% and glucosamine in the range of 0.5%-8% in the first part with the balance consisting of water or a physiologically compatible buffer. A most preferred embodiment of the invention contains approximately gelatin 17.5%, urea 17.5% and chitosan in the range of 0.1%-0.5% and glucosamine in the range of 0.5%-6% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately gelatin 35%, urea 35% and dextran (mw 40,000-150,000 da) in the range of 0.001%-5% in the first part with the balance consisting of water or a physiologically compatible buffer. A more preferred embodiment of the invention contains approximately gelatin 25%, urea 25% and dextran (mw 40,000-150,000 da) in the range of 0.05%-4% in the first part with the balance consisting of water or a physiologically compatible buffer. A most preferred embodiment of the invention contains approximately gelatin 20%, urea 20% and dextran (mw 40,000-150,000 da) in the range of 0.5%-3% in the first part with the balance consisting of water or a physiologically compatible buffer. A most preferred embodiment of the invention contains approximately gelatin 17.5%, urea 17.5% and dextran (mw 40,000-150,000 da) in the range of 0.5%-3% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second component.

Another preferred embodiment of the invention contains approximately gelatin 35%, urea 35% and dextran (mw 40,000-150,000 da) in the range of 0.001%-5% alternatively with vanillin 0.001%-5% in the first component with the balance consisting of water or a physiologically compatible buffer. A more preferred embodiment of the invention contains approximately gelatin 25%, urea 25% and dextran (mw 40,000-150,000 da) in the range of 0.05%-4% alternatively with vanillin 0.01%-4% in the first part with the balance consisting of water or a physiologically compatible buffer. A most preferred embodiment of the invention contains approximately gelatin 20%, urea 20% and dextran (mw 40,000-150,000 da) in the range of 0.5%-3% alternatively with vanillin 0.1%-3% in the first part with the balance consisting of water or a physiologically compatible buffer. A most preferred embodiment of the invention contains approximately gelatin 17.5%, urea 17.5% and dextran (mw 40,000-150,000 da) in the range of 0.5%-3% alternatively with vanillin 0.5%-3% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately gelatin 35%, urea 35% and dextran (mw 40,000-150,000 da) in the range of 0.001%-5% alternatively with glucosamine 0.001%-15% in the first part with the balance consisting of water or a physiologically compatible buffer. A more preferred embodiment of the invention contains approximately gelatin 25%, urea 25% and dextran (mw 40,000-150,000 da) in the range of 0.05%-4% alternatively with glucosamine 0.05%-12% in the first part with the balance consisting of water or a physiologically compatible buffer. A most preferred embodiment of the invention contains approximately gelatin 20%, urea 20% and dextran (mw 40,000-150,000 da) in the range of 0.5%-3% alternatively with glucosamine 0.5%-8% in the first part with the balance consisting of water or a physiologically compatible buffer. A most preferred embodiment of the invention contains approximately gelatin 17.5%, urea 17.5% and dextran (mw 40,000-150,000 da) in the range of 0.5%-3% alternatively with glucosamine 0.5%-6% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second component. A more preferred embodiment of the invention contains approximately 0.1-5% glutaraldehyde in an aqueous buffer system in the second component. A most preferred embodiment of the invention contains approximately 0.1-2.5% glutaraldehyde in an aqueous buffer system in the second component.

Another preferred embodiment of the invention contains approximately gelatin 35%, urea 35% and chitosan in the range of 0.001%-5% and dextran (mw 40,000-150,000 da) in the range of 0.001%-5% alternatively with vanillin 0.001%-5% in the first part with the balance consisting of water or a physiologically compatible buffer. A more preferred embodiment of the invention contains approximately gelatin 25%, urea 25% and chitosan in the range of 0.005%-3% and dextran (mw 40,000-150,000 da) in the range of 0.05%-4% alternatively with vanillin 0.005%-4% in the first part with the balance consisting of water or a physiologically compatible buffer. A most preferred embodiment of the invention contains approximately gelatin 20%, urea 20% and chitosan in the range of 0.075%-2% and dextran (mw 40,000-150,000 da) in the range of 0.5%-3% alternatively with vanillin 0.5%-3% in the first part with the balance consisting of water or a physiologically compatible buffer. A most preferred embodiment of the invention contains approximately gelatin 17.5%, urea 17.5% and chitosan in the range of 0.1%-0.5% and dextran (mw 40,000-150,000 da) in the range of 0.5%-3% alternatively with vanillin 0.5%-3% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately gelatin 35%, urea 35%, chitosan in the range of 0.001%-5% and dextran (mw 40,000-150,000 da) in the range of 0.001%-5%, glucosamine in the range of 0.001%-15% alternatively with vanillin 0.001%-5% in the first part with the balance consisting of water or a physiologically compatible buffer. A more preferred embodiment of the invention contains approximately gelatin 25%, urea 25%, chitosan in the range of 0.005%-3% and dextran (mw 40,000-150,000 da) in the range of 0.05%-4%, glucosamine in the range of 0.05%-12% alternatively with vanillin 0.005%-4% in the first part with the balance consisting of water or a physiologically compatible buffer. A most preferred embodiment of the invention contains approximately gelatin 20%, urea 20%, chitosan in the range of 0.075%-2% and dextran (mw 40,000-150,000 da) in the range of 0.5%-3%, glucosamine in the range of 0.5%-8% alternatively with vanillin 0.5%-3% in the first part with the balance consisting of water or a physiologically compatible buffer. A most preferred embodiment of the invention contains approximately gelatin 17.5%, urea 17.5%, chitosan in the range of 0.1%-0.5%, dextran (mw 40,000-150,000 da) in the range of 0.5%-3%, glucosamine in the range of 0.5%-6% alternatively with vanillin 0.5%-3% in the first component with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately albumin 45%, urea 0-20% and chitosan in the range of 0.001%-25% in the first part with the balance consisting of water or a physiologically compatible buffer. A more preferred embodiment of the invention contains approximately albumin 40%, urea 0-15% and chitosan in the range of 0.005%-7.5% in the first part with the balance consisting of water or a physiologically compatible buffer. A most preferred embodiment of the invention contains approximately albumin 35%, urea 0-10% and chitosan in the range of 0.075%-5% in the first part with the balance consisting of water or a physiologically compatible buffer. A most preferred embodiment of the invention contains approximately albumin 35%, urea 0-5% and chitosan in the range of 0.075%-3% in the first part with the balance consisting of water or a physiologically compatible buffer. A most preferred embodiment of the invention contains approximately albumin 35%, urea 0-5% and chitosan in the range of 0.075%-3% in the first part with the balance consisting of water or a physiologically compatible buffer. A most preferred embodiment of the invention contains approximately albumin 25%, urea 0-5% and chitosan in the range of 0.075%-3% in the first part with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 15% glutaraldehyde in an aqueous buffer system in the second part. A most preferred embodiment of the invention contains approximately 0.1-15% glutaraldehyde in an aqueous buffer system in the second part. A most preferred embodiment of the invention contains approximately 0.1-10% glutaraldehyde in an aqueous buffer system in the second part. A most preferred embodiment of the invention contains approximately 0.1-5% glutaraldehyde in an aqueous buffer system in the second part.

Another preferred embodiment of the invention contains approximately albumin 35%, urea 0-10% and chitosan in the range of 0.001%-10% in the first part with the balance consisting of water or a physiologically compatible buffer. A more preferred embodiment of the invention contains approximately albumin 30%, urea 0-7.5% and chitosan in the range of 0.005%-5% in the first part with the balance consisting of water or a physiologically compatible buffer. A most preferred embodiment of the invention contains approximately albumin 25%, urea 0-5% and chitosan in the range of 0.075%-7.5% in the first part with the balance consisting of water or a physiologically compatible buffer. A most preferred embodiment of the invention contains approximately albumin 20%, urea 0-5% and chitosan in the range of 0.075%-7.5% in the first part with the balance consisting of water or a physiologically compatible buffer. A most preferred embodiment of the invention contains approximately albumin 15%, urea 0-5% and chitosan in the range of 0.075%-7.5% in the first part with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A most preferred embodiment of the invention contains approximately 0.1-10% glutaraldehyde in an aqueous buffer system in the second part. A most preferred embodiment of the invention contains approximately 0.1-4% glutaraldehyde in an aqueous buffer system in the second part. A most preferred embodiment of the invention contains approximately 0.1-2.5% glutaraldehyde in an aqueous buffer system in the second part.

The embodiments are further described by the following aspects:
1. A composition useful as a tissue sealant, tissue dressing, tissue barrier or tissue adhesive comprising: (a) a compound or composition selected from the group of a Monomer, a Polymer, derivatives of this group or any combination thereof; (b) a cross-linking agent; and (c) a Modifier or any combination of Modifiers.
2. A composition according to item 1 wherein the compound (a) is selected from the group of biological macromolecules including proteins, peptides, poly amino acids, lipids, phospholipids; polysaccharides, polyamine acids, polyesters, polyortho esters, polyanhydrides, polyphosphazines, derivatives of this group or any combination thereof.
3. A composition according to item 2, wherein the compound (a) is selected from the group consisting of lactoferrin, lactalbumin, albumin, bovine serum albumin, human serum albumin, gelatin, gelatin hydrolysates, casein, collagen, fibrinogen, gliadin, bacterial enzymes, derivatives of this group or any combination thereof.
4. A composition according to item 2, wherein the compound (a) is selected from the group consisting of alginates, chitin, chitosan, cellulose, starch, dextran, hyaluronic acid, gums, lignins, pectins, cyclodextrins, derivatives of this group or any combination thereof.
5. A composition according to item 1 wherein the Modifier is a Gelation Disrupting Agent (c) is selected from the group of an acid, an alkali compound, an ionic compound, urea, sulfonylurea, derivatives of this group or any combination thereof.
6. A composition according to item 1 wherein the cross-linking agent (b) is selected from the group consisting of an aldehyde compound, a polyaldehyde compound, formaldehyde, glutaraldehyde, acetaldehyde, malonaldehyde, succinaldehyde, adipaldehyde, dialdehyde starch, glyoxal, glyoxylic acid, adipyldichloride, acrolein, N,N'-methylenebisacrylamide, N,N'-ethylenebisacrylamide, (poly)ethylene glycol di(meth)acrylate, ethylene glycol diglycidyl ether, glycidyl methacrylate, polyamidoamine epichlorohydrin, trimethylolpropane triacrylate, piperazine diacrylamide, epichlorohydrin, 1,2-diol compounds, functionalized peptides and proteins, tannins, derivatives of this group or any combination thereof.
7. A composition according to item 1 wherein the Modifier is an Adjunct Compound or agent (d) is selected from the group consisting of chitin, chitosan, a cellulosic, starch, dextran, a gum, a lignin, a pectin, hyaluronic acid, a glucosamine, N-acetyl glucosamine, resorcinol, vanillin, nicotinamide, a polyacrolein, a poly(acrylic acid), polyacrylonitrile, a polyacrylamide, a poly amino acids, a polyvinylpyrrolidone, a polyvinyl alcohol, a methacrylic acid polymer, and a poly(ethylene glycol), derivatives of this group or any combination thereof.
8. A composition according to item 3 wherein the gelatin is present in a concentration range of 5%-50% prior to combining or a theoretical 1%-35% after combining.
9. A composition according to item 3 wherein the albumin is present in a concentration range of 5%-50% prior to combining or a theoretical 1%-45% after combining.
10. A composition according to item 3 wherein the lactoferrin is present in a concentration range of 5%-50% prior to combining or a theoretical 1%-45% after combining.
11. A composition according to item 5 wherein urea is present in a concentration range of 0-30% prior to combining or a theoretical 0%-25% after combining.
12. A composition according to item 6 wherein glutaraldehyde is utilized in a concentration range of 0.5%-25% prior to combining or a theoretical 0.1%-10% after combining.
13. A composition according to item 7 wherein chitosan is present in a concentration range of 0.005%-25% prior to combining or a theoretical 0.005%-20% after combining.
14. A composition according to item 7 wherein the dextran is present in a concentration range of 0.005%-25% prior to combining or a theoretical 0.005%-20% after combining.
15. A composition according to item 7 wherein glucosamine is present in a concentration range of 0.005%-25% prior to combining or a theoretical 0.005%-20% after combining.
16. A composition useful as a tissue sealant, tissue dressing, tissue barrier or tissue adhesive comprising: (a) an amino acid containing compound or composition selected from the group of proteins, peptides, poly amino acids, protein hydrolysates, peptide hydrolysates, derivatives of this group or any combination thereof; (b) a cross-linking agent; and (c) a modifier or any combination of modifiers.
17. A composition according to item 16, wherein the amino acid derivative (a) is selected from the group consisting of lactoferrin, lactalbumin, albumin, bovine serum albumin, human serum albumin, gelatin, gelatin hydrolysates, casein, collagen, fibrinogen, gliadin, bacterial enzymes, derivatives of this group or any combination thereof.

18. A composition according to item 16 wherein the cross-linking agent (b) is selected from the group consisting of an aldehyde compound, a polyaldehyde compound, formaldehyde, glutaraldehyde, acetaldehyde, malonaldehyde, succinaldehyde, adipaldehyde, dialdehyde starch; glyoxal, glyoxylic acid, adipyldichloride, acrolein, N,N'-methylenebisacrylamide, N,N'-ethylenebisacrylamide, (poly)ethylene glycol di(meth)acrylate, ethylene glycol diglycidyl ether, glycidyl methacrylate, polyamidoamine epichlorohydrin, trimethylolpropane triacrylate, piperazine diacrylamide, epichlorohydrin, 1,2-diol compounds, functionalized peptides and proteins, tannins, derivatives of this group or any combination thereof.

19. The composition of item 16 wherein the modifier is a gelation disrupting agent selected from the group of an acid, an alkali compounds, an ionic compound, urea, sulfonylurea, a derivative of this group or any combination thereof.

20. The composition of item 16 wherein the modifier is an augmentative polymer or monomer containing reactive sites selected from the group of a nitrogen containing site, a sulfur containing site, or any combination thereof.

21. The composition of item 20 wherein the modifier is an augmentative polymer or monomer selected from the group of chitin, chitosan, glucosamine, N-acetyl glucosamine, hyaluronic acid, sulfoglucosamine, chondroitin, adenosine, an aminoglycoside, glycosylamine, galactosamine, a derivative of this group or any combination thereof.

22. A composition according to item 16 wherein the modifier is an adjunct compound or agent selected from the group consisting of chitin, chitosan, cellulose, starch, dextran, gums, lignins, pectins, hyaluronic acid, resorcinol, vanillin, nicotinamide, polyacrolein, poly(acrylic acid), polyacrylonitrile, polyacrylamide, poly amino acids, polyvinylpyrrolidone, polyvinyl alcohol, methacrylic acid polymers, and poly(ethylene glycol), derivatives of this group or any combination thereof.

23. The composition of item 16 wherein the modifier is an antimicrobial selected from the group of urea, a lipid compound, a silver compound, lactoferrin, lysozyme, sulfonamide, sulfamethoxazole, a sugar, a sugar alcohol, xylitol, methylene blue, gentian violet, an aminoglycoside, a derivative of this group, or any combination thereof.

24. The composition of item 16 wherein the modifier is an adhesion enhancer selected from the group of a natural polymer including polysaccharides, dextran, a dextrin, a cellulosic, a synthetic polymer including poly vinyl derivatives, polyvinyl pyrrolidone, derivatives of this group or any combination thereof.

25. The composition of item 16 wherein the modifier is a crosslink augmentating agent selected from the group of polyhydroxybenzene, resorcinol, vanillin, nicotinamide, adenosine, a derivative of this group or any combination thereof.

26. A method for effectively sealing, coating and adhering tissues at a desired site of a subject, the method comprising administering by positive pressure an effective amount of a formulation comprising: (a) a compound or composition selected from the group of a monomer, a polymer, derivatives of this group or any combination thereof; (b) a cross-linking agent; and (c) a modifier or any combination of modifiers, at the site for a period of time effective to seal, coat or adhere the tissue at the site.

27. A method for effectively sealing, coating and adhering tissues at a desired site of a subject, the method comprising administering by positive pressure an effective amount of a formulation comprising: (a) an amino acid containing compound or composition selected from the group of proteins, peptides, poly amino acids, protein hydrolysates, peptide hydrolysates, derivatives of this group or any combination thereof; (b) a cross-linking agent; and (c) a Modifier or any combination of modifiers, at the site for a period of time effective to seal, coat or adhere the tissue at the site.

II. Compositions & Methods Dependent on Lactoferrin

Broadly preferred compositions and methods are disclosed which significantly improve at least one critical attribute of a sealant or adhesive including strength, resilience, toxicity, swelling, infection rates, ease of use, variability, allergic potential, degradation rate and the risk of disease by transmission. The compositions and methods utilize multiple parts initially which are combined just prior to or during applications via several delivery methodologies.

A first best mode of the invention involves the utility of a lactoferrin derivative and a crosslinking agent, which is a composition with significant improvements of critical attributes relative to the prior art.

In second best mode, the invention involves the utility of a lactoferrin derivative, crosslinking agent and at least one modifier, which allows further improvement of critical attributes.

One method of the invention may be operated by administering by positive pressure an effective amount of a formulation comprising: (a) a lactoferrin derivative or any combination thereof and (b) a cross-linking agent, at the site for a period of time effective to seal, coat or adhere the tissue at the site. Another method of the invention may be operated by administering by positive pressure an effective amount of a formulation comprising: (a) a lactoferrin derivative or any combination thereof; (b) a cross-linking agent; and (c) a modifier or any combination of modifiers, at the site for a period of time effective to seal, coat or adhere the tissue at the site. Another method of the invention may be operated by substituting lactoferrin or lactoferrin derivatives, optionally from recombinant or a non-bovine source, for problematic bovine proteins including albumin, collagen, collagen hydrolysates or gelatin; thereby lowering the risk of transmitting an infecting agent including bovine spongiform encephalopathy.

Another preferred embodiment of the invention contains approximately lactoferrin 45%, urea 0-20% and chitosan in the range of 0.001%-25% in the first part with the balance consisting of water or a physiologically compatible buffer. A more preferred embodiment of the invention contains approximately lactoferrin 40%, urea 0-15% and chitosan in the range of 0.005%-7.5% in the first part with the balance consisting of water or a physiologically compatible buffer. A most preferred embodiment of the invention contains approximately lactoferrin 35%, urea 0-10% and chitosan in the range of 0.075%-5% in the first part with the balance consisting of water or a physiologically compatible buffer. A most preferred embodiment of the invention contains approximately lactoferrin 35%, urea 0-5% and chitosan in the range of 0.075%-3% in the first part with the balance consisting of water or a physiologically compatible buffer. A most preferred embodiment of the invention contains approximately lactoferrin 35%, urea 0-5% and chitosan in the range of 0.075%-3% in the first part with the balance consisting of water or a physiologically compatible buffer. A most preferred embodiment of the invention contains approximately lactoferrin 25%, urea 0-5% and chitosan in the range of 0.075%-3% in the first part with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A most preferred embodiment of the invention contains approximately 0.1-10% glutaraldehyde in an aqueous buffer system in the second part. A most preferred embodiment of the invention contains approximately 0.1-5% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately lactoferrin 35%, urea 0-10% and chitosan in the range of 0.001%-25% in the first part with the balance consisting of water or a physiologically compatible buffer. A more preferred embodiment of the invention contains approximately lactoferrin 30%, urea 0-7.5% and chitosan in the range of 0.005%-7.5% in the first part with the balance consisting of water or a physiologically compatible buffer. A most preferred embodiment of the invention contains approximately lactoferrin 25%, urea 0-5% and chitosan in the range of 0.075%-3% in the first part with the balance consisting of water or a physiologically compatible buffer. A most preferred embodiment of the invention contains approximately lactoferrin 20%, urea 0-5% and chitosan in the range of 0.075%-3% in the first part with the balance consisting of water or a physiologically compatible buffer. A most preferred embodiment of the invention contains approximately lactoferrin 15%, urea 0-5% and chitosan in the range of 0.075%-3% in the first part with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A most preferred embodiment of the invention contains approximately 0.1-10% glutaraldehyde in an aqueous buffer system in the second part. A most preferred embodiment of the invention contains approximately 0.1-4% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately lactoferrin 45% in the first part with the balance consisting of water or a physiologically compatible buffer. A most preferred embodiment of the invention contains approximately lactoferrin 40% in the first part with the balance consisting of water or a physiologically compatible buffer. A most preferred embodiment of the invention contains approximately lactoferrin 35% in the first part with the balance consisting of water or a physiologically compatible buffer. A most preferred embodiment of the invention contains approximately lactoferrin 25% in the first part with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-4% glutaraldehyde in an aqueous buffer system in the second part. A most preferred embodiment of the invention contains approximately 0.1-2.5% glutaraldehyde in an aqueous buffer system in the second part.

Another preferred embodiment of the invention contains approximately lactoferrin 25% in the first part with the balance consisting of water or a physiologically compatible buffer. A more preferred embodiment of the invention contains approximately lactoferrin 20% in the first part with the balance consisting of water or a physiologically compatible buffer. A most preferred embodiment of the invention contains approximately lactoferrin 15% in the first part with the balance consisting of water or a physiologically compatible buffer. A most preferred embodiment of the invention contains approximately lactoferrin 10% in the first part with the balance consisting of water or a physiologically compatible buffer. A most preferred embodiment of the invention contains approximately lactoferrin 7.5% in the first part with the balance consisting of water or a physiologically compatible buffer. A preferred embodiment of the invention contains approximately 25% glutaraldehyde in an aqueous buffer system in the second part. A more preferred embodiment of the invention contains approximately 20% glutaraldehyde in an aqueous buffer system in the second part. A more preferred embodiment of the invention contains approximately 0.1-15% glutaraldehyde in an aqueous buffer system in the second part. A more preferred embodiment of the invention contains approximately 0.1-10% glutaraldehyde in an aqueous buffer system in the second part. A more preferred embodiment of the invention contains approximately 0.1-4% glutaraldehyde in an aqueous buffer system in the second part. A most preferred embodiment of the invention contains approximately 0.1-2.5% glutaraldehyde in an aqueous buffer system in the second part.

The embodiments are further described by the following aspects:

28. A composition useful as a tissue sealant, tissue dressing, tissue barrier or tissue adhesive comprising: (a) an amino acid containing compound or composition selected from the group of lactoferrin, lactoferrin peptides, lactoferrin hydrolysates, derivatives of this group or any combination thereof; and (b) a cross-linking agent; and optionally, (c) a Modifier or any combination of Modifiers.

29. A composition according to item 28 wherein the cross-linking agent (b) is selected from the group consisting of an aldehyde compound, a polyaldehyde compound, formaldehyde, glutaraldehyde, acetaldehyde, malonaldehyde, succinaldehyde, adipaldehyde, dialdehyde starch, glyoxal, glyoxylic acid, adipyldichloride, acrolein, N,N'-methylenebisacrylamide, N,N'-ethylenebisacrylamide, (poly)ethylene glycol di(meth)acrylate, ethylene glycol diglycidyl ether, glycidyl methacrylate, polyamidoamine epichlorohydrin, trimethylolpropane triacrylate, piperazine diacrylamide, glutaraldehyde, epichlorohydrin, 1,2-diol compounds, functionalized peptides and proteins, tannins, derivatives of this group or any combination thereof.

30. A method for effectively Sealing, coating and adhering tissues at a desired site of a subject, the method comprising administering by positive pressure an effective amount of a formulation comprising: (a) an amino acid containing compound or composition selected from the group of lactoferrin, lactoferrin peptides, lactoferrin hydrolysates, derivatives of this group or any combination thereof; and (b) a cross-linking agent; and optionally, (c) a Modifier or any combination of Modifiers, at the site for a period of time effective to Seal, coat or adhere the tissue at the site.

III. Production Methods

Broadly preferred manufacturing methods are disclosed which significantly improve the efficiency, convenience and output of manufacturing the sealants and adhesives disclosed herein. The methods utilize and initial heating step universally.

The best mode of the invention utilizes the following steps (a) preparing at least one component by heating to a temperature of 35-150 degrees C.; and (b) completing this preparation stage with a regimen selected from the group of (i) allowing the composition to return to ambient temperature, (ii) cooling to about 4-10 degrees C. before returning to ambient temperature, (iii) allowing the composition to return to ambient temperature, and then adding additional components if utilized excluding the crosslinking agent, (iv) adding additional components if utilized excluding the crosslinking agent while above ambient temperature, or (v) cooling to about 4-10 degrees C. before returning to ambient temperature before adding any additional components if utilized excluding the crosslinking agent.

A method of producing one or more of the preferred embodiments involves combination of the materials of the first part utilizing a protein and a Gelation Disrupting Agent as examples with the balance of water or buffer necessary for proper concentrations or each. This portion of the part is then heated to approximately 30°-60° C. for approximately 15 minutes to 2 hrs with intermittent mixing. This portion of the part is then removed from the heat source and additional parts may be added in dry state or solution as necessary. The part can then be allowed to return to ambient temperature prior to utilization as described herein elsewhere. Alternatively, the part may be stored at approximately 4° C.-15° C. for further conditioning of the composition. The material may be utilized at the reduced temperature or allowed to return to ambient temperature prior to utilization as described herein.

The embodiments are further described by the following aspects:

31. A method of manufacturing the formulation components of sealant, coating and adhesive compositions disclosed herein comprising (a) preparing at least one component by heating to a temperature of 35-150 degrees C.; and (b) completing this preparation stage with a regimen selected from the group of (i) allowing the composition to return to ambient temperature, (ii) cooling to about 4-10 degrees C. before returning to ambient temperature, (iii) allowing the composition to return to ambient temperature before adding additional components if utilized but excluding the crosslinking agent, (iv) adding additional components if utilized but excluding the crosslinking agent while above ambient temperature, or (v) cooling to about 4-10 degrees C. before returning to ambient temperature, and then adding any additional components if utilized excluding the crosslinking agent.

IV. Methods of Delivery:

Broadly preferred delivery methods are disclosed which significantly improve the convenience and ease of use when applying the sealants and adhesives disclosed herein. The methods utilize various ordered steps and terminal delivery tips to provide a delivery method catered to the medical application.

A first best mode of the invention utilizes the following key delivery steps [1] providing one part at least composed of component (a); [2] providing at least another part composed of component (b); and [3] completing the delivery with a regimen selected from the group of (i) mixing the separate parts by mechanical or fluid means prior to application, (ii) mixing the separate parts by mechanical or fluid means during application, or (iii) applying one part to the treatment site and subsequently any remaining parts to the desired treatment site to form a Seal, a coating or an adhesion within or between tissues of the body.

A second best mode of the invention utilizes the following key delivery steps [1] providing one part at least composed of component (a); [2] providing at least another part composed of component (b); and [3] completing the delivery with a regimen selected from the group of (i) mixing the parts to create a final mixture and atomizing the final mixture in less than 2 minutes, or (ii) atomizing the separate parts together creating a final mixture via atomization.

A third best mode of the invention utilizes a key delivery step comprising utilizing a mixing tip in single phase or alternating phase configuration selected from the group of (i) an auger; (ii) a zigzag; (iii) a baffle or (iv) a swirl to mix the parts just prior to contact with the site of application.

A fourth best mode of the invention utilizes a key delivery step comprising utilizing a spray tip in a configuration selected from the group of (i) a dual liquid feed, and optionally a dual port, with air atomization; (ii) a dual liquid feed with hydraulic atomization; or (iii) a coaxial liquid feed, and optionally a dual port, with air or hydraulic atomization to combine the components during application to desired site.

A method of the invention comprises applying the preferred compositions by: (a) preparing the components into at least two parts and, optionally, pre-mixing at least some of the components; (b) mixing the multiple parts to create a final mixture; and (c) atomizing the final mixture in less than 2 minutes of combining the parts.

A method of the invention comprises applying the preferred compositions by: (a) preparing the components into multiple parts and, optionally, pre-mixing at least some of the parts but keeping at least two parts separate; and (b) atomizing the separate parts together creating a final mixture via atomization.

A method of the invention comprises applying the preferred compositions by employing (a) an auger mixing tip, (b) a zigzag mixing tip, (c) a swirl mixing tip, (d) a baffle mixing tip, (e) a dual liquid port with air atomization, (f) a dual liquid port with hydraulic atomization or (g) a coaxial mixing tip with atomization.

The embodiments are further described by the following aspects:

32. A method of delivering the sealant, coating and adhesive compositions disclosed herein at a desired site of a subject as initially a multiple part system comprising: [1] providing one part is at least composed of component (a); [2] providing at least another part composed of component (b); and [3] completing the delivery with a regimen selected from the group of (i) mixing the separate parts by mechanical or fluid means prior to application, (ii) mixing the separate parts by mechanical or fluid means during application, or (iii) applying one part to the treatment site and subsequently any remaining parts to the desired treatment site to form a Seal, a coating or an adhesion within or between tissues of the body.

33. A method of delivering the sealant, coating and adhesive compositions disclosed herein at a desired site of a subject as initially a multiple part system comprising: [1] providing one part is at least composed of component (a); [2] providing at least another part composed of component (b); and [3] completing the delivery with a regimen selected from the group of (i) mixing the parts to create a final mixture and atomizing the final mixture in less than 2 minutes, or (ii) atomizing the separate parts together creating a final mixture via atomization.

34. The method of item 33 wherein the atomization is achieved by an ultrasonic nozzle.

35. The method of item 33 wherein the atomization is achieved by air or pressurized gas.

36. The method of item 33 wherein the atomization is achieved by hydraulic pressure.

37. The method of item 33 wherein the parts are mixed just prior to atomization or during atomization.

38. A method of delivering the sealant, coating and adhesive compositions disclosed herein at a desired site of a subject comprising utilizing a mixing tip in single phase or alternating phase configuration selected from the group of (i) an auger; (ii) a zigzag; (iii) a baffle or (iv) a swirl to mix the parts just prior to contact with the site of application.

39. A method of delivering the sealant, coating and adhesive compositions disclosed herein at a desired site of a subject comprising utilizing a spray tip in a configuration selected from the group of (i) a dual liquid feed, and optionally a dual port, with air atomization; (ii) a dual liquid feed with hydraulic atomization; or (iii) a coaxial liquid feed, and optionally a dual port, with air or hydraulic atomization to combine the components during application to desired site.

All such variations are intended to be within the scope and spirit of the invention. Although some embodiments are shown to include certain features, the applicant(s) specifically contemplate that any feature disclosed herein may be used together or in combination with any other feature on any embodiment of the invention. It is also contemplated that any feature may be specifically excluded from any embodiment of an invention. With the invention now described, it will be apparent to one of ordinary skill in the art that many changes and modifications can be made thereto without departing from the spirit or scope of the appended claims.

Example 1

| Part One | |
|---|---|
| 1. Gelatin | 20% |
| 2. Urea | 20% |
| 3. Water | 60% |
| Part Two | |
| 1. Glutaraldehyde | 2.5% |
| 2. Water | 97.5% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 3 min of application by in vitro tissue models. This example delivered in a 1:1 ratio forms a sealant or anti-adhesive mass within 4 min of application. In vivo models showed relatively faster biodegradation. The formulations are biodegradable and particularly adapted to use as a vascular tissue sealant, dural sealant or tissue anti-adhesion barrier.

Example 2

| Part One | |
|---|---|
| 1. Gelatin | 20.00% |
| 2. Urea | 20.00% |
| 3. Chitosan | 0.15% |
| 4. Water | 59.85% |
| Part Two | |
| 1. Glutaraldehyde | 2.50% |
| 2. Water | 97.50% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 2 min of application to an in vitro tissue model. This example delivered in a 1:1 ratio forms a sealant or anti-adhesive mass within 3 min of application. In vivo models showed relatively faster biodegradation. The formulations are biodegradable and particularly adapted to use as a vascular tissue sealant, dural sealant or tissue anti-adhesion article.

Example 3

| Part One | |
|---|---|
| 1. Gelatin | 20.00% |
| 2. Urea | 20.00% |
| 3. Chitosan | 0.15% |
| 4. Glucosamine | 1.00% |
| 5. Water | 58.85% |
| Part Two | |
| 1. Glutaraldehyde | 2.50% |
| 2. Water | 97.50% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 1.5 min of application to renal slice and aortic puncture models in rabbits. This example delivered in a 1:1 ratio forms a sealant or anti-adhesive mass within 2 min of application. In vivo models showed relatively faster biodegradation. The formulations are biodegradable and particularly adapted to use as a vascular tissue sealant, dural sealant or tissue anti-adhesion article.

Example 4

| Part One | |
|---|---|
| 1. Gelatin | 20.00% |
| 2. Urea | 20.00% |
| 3. Chitosan | 0.30% |
| 4. Glucosamine | 1.00% |
| 5. Water | 58.70% |
| Part Two | |
| 1. Glutaraldehyde | 2.50% |
| 2. Water | 97.50% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 1.5 min of application to an in vitro tissue model. This example delivered in a 1:1 ratio forms a sealant or anti-adhesive mass within 2 min of application. In vivo models showed relatively faster biodegradation. The formulations are biodegradable and particularly adapted to use as a vascular tissue sealant, dural sealant or tissue anti-adhesion article.

Example 5

| Part One | |
|---|---|
| 1. Gelatin | 20.00% |
| 2. Urea | 20.00% |
| 3. Chitosan | 0.15% |
| 4. Dextran | 2.00% |
| 5. Water | 57.85% |
| Part Two | |
| 1. Glutaraldehyde | 2.50% |
| 2. Water | 97.50% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 2 min of application to an in vitro tissue model. This example delivered in a 1:1 ratio forms a sealant or anti-adhesive mass within 3 min of application. In vivo models showed relatively faster biodegradation. The formulations are biodegradable and particularly adapted to use as a vascular tissue sealant, dural sealant or tissue anti-adhesion article.

Example 6

| Part One | |
|---|---|
| 1. Gelatin | 20.00% |
| 2. Urea | 20.00% |
| 3. Chitosan | 0.15% |
| 4. Vanillin | 3.00% |
| 5. Water | 56.85% |
| Part Two | |
| 1. Glutaraldehyde | 2.50% |
| 2. Water | 97.50% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 2 min of application to an in vitro tissue model. This example delivered in a 1:1 ratio forms a sealant or anti-adhesive mass within 3 min of application. In vivo models showed relatively faster biodegradation. The formulations are biodegradable and particularly adapted to use as a vascular tissue sealant, dural sealant or tissue anti-adhesion article.

Example 7

| Part One | |
|---|---|
| 1. Bovine Serum Albumin | 35.00% |
| 2. Urea | 5.00% |
| 3. Water | 60.00% |
| Part Two | |
| 1. Glutaraldehyde | 10.00% |
| 2. Water | 90.00% |
| Combining Ratio of Parts (Part One:Part Two) | |
| 4:1 & 1:1 | |
| Delivery/Application Method | |
| 4:1- Dual syringe with auger mixing tip | |
| 1:1- Dual syringe atomization-spray | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 1 min of application to an in vitro tissue model. This example delivered in a 1:1 ratio forms a sealant or anti-adhesive mass within 2.5 min of application.

The formulations are biodegradable and particularly adapted to use as a vascular tissue sealant. In addition due to the limited multidimensional swelling of the example, it is also particularly adapted for use as a dural sealant.

Example 8

| Part One | |
| --- | --- |
| 1. Bovine Serum Albumin | 35.00% |
| 2. Urea | 5.00% |
| 3. Chitosan | 0.15% |
| 4. Water | 59.85% |
| Part Two | |
| 1. Glutaraldehyde | 10.00% |
| 2. Water | 90.00% |
| Combining Ratio of Parts (Part One:Part Two) | |
| 4:1 & 1:1 | |
| Delivery/Application Method | |
| 4:1- Dual syringe with auger mixing tip | |
| 1:1- Dual syringe atomization-spray | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 0.5-1 min of application to renal slice and aortic puncture models in rabbits. This example delivered in a 1:1 ratio forms a sealant or anti-adhesive mass within 1.5-2 min of application. In vitro models demonstrated significantly lower strength and resilience variability for this example. For the current example, increasing the chitosan content further reduced variability. The formulations are biodegradable and particularly adapted to use as a vascular tissue sealant. In addition due to the limited multidimensional swelling of the example, it is also particularly adapted for use as a dural sealant. Bacteriocidal Testing: The formulation (4:1 dual syringe with auger mixing tip) was placed in a 24-well plate and allowed to cure for 48 hr prior to bacterial challenge with $1 \times 10^5$ cfu/ml of Staph Aureus followed by 6 hr incubation. Samples of uncured formulations were challenged with $1 \times 10^5$ cfu/ml of Staph Aureus followed by 10 min incubation. The present example produced a 3.13 log reduction in bacteria following a 48 hr cure and 6 hr incubation compared to control. Samples of uncured formulations produced a 1.4 log reduction in bacteria following a 10 min incubation compared to control.

Example 9

| Part One | |
| --- | --- |
| 1. Bovine Serum Albumin | 35.00% |
| 2. Urea | 5.00% |
| 3. Chitosan | 0.15% |
| 4. Water | 59.85% |
| Part Two | |
| 1. Glutaraldehyde | 5.00% |
| 2. Water | 95.00% |
| Combining Ratio of Parts (Part One:Part Two) | |
| 4:1 & 1:1 | |
| Delivery/Application Method | |
| 4:1- Dual syringe with auger mixing tip | |
| 1:1- Dual syringe atomization-spray | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 1.5 min of application to an in vitro tissue model. This example delivered in a 1:1 ratio forms a sealant or anti-adhesive mass within 2 min of application. In vivo models showed relatively faster biodegradation. In vitro models demonstrated significantly lower strength and resilience variability for this example. For the current example, increasing the chitosan content further reduced variability. The formulations are biodegradable and particularly adapted to use as a vascular tissue sealant. In addition due to the limited multidimensional swelling of the example, it is also particularly adapted for use as a dural sealant. Swelling Studies: Cylindrical devices of the formulation were produced by dispensing the formulation into a uniform mold and allowing the system to cure for 15 min. Following curing, devices were removed and placed in 0.05 M phosphate buffered saline (pH 7.4) at 37° C. the average changes in weight, length and width for the 4:1 ratio were 13.88%, 6.22%, and 4.86% respectively over a 5 day period of time from the measurements at t=0.

Example 10

| Part One | |
| --- | --- |
| 1. Bovine Serum Albumin | 35.00% |
| 2. Urea | 5.00% |
| 3. Chitosan | 0.15% |
| 4. Water | 59.85% |
| Part Two | |
| 1. Glutaraldehyde | 4.00% |
| 2. Water | 96.00% |
| Combining Ratio of Parts (Part One:Part Two) | |
| 1:1 | |
| Delivery/Application Method | |
| Hydraulic atomization tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 1.5 min of application to an in vitro tissue model. In vivo models showed relatively faster biodegradation. In vitro models demonstrated significantly lower strength and resilience variability for this example. For the current example, increasing the chitosan content further reduced variability. The formulation is biodegradable and particularly adapted to use as a vascular tissue sealant. In addition due to the limited multidimensional swelling of the example, it is also particularly adapted for use as a dural sealant. Swelling Studies: Cylindrical devices of the formulation were produced by dispensing the formulation into a uniform mold and allowing the system to cure for 15 min. Following curing, devices were removed and placed in 0.05 M phosphate buffered saline (pH 7.4) at 37° C. the average changes in weight, length and width were 16.7%, 4.9%, and 1.3% respectively over a 5 day period of time from the measurements at t=0.

Example 11

| Part One | |
| --- | --- |
| 1. Bovine Serum Albumin | 25.00% |
| 2. Urea | 5.00% |
| 3. Chitosan | 0.15% |
| 4. Glucosamine | 1.00% |
| 5. Water | 68.85% |
| Part Two | |
| 1. Glutaraldehyde | 2.50% |
| 2. Water | 97.50% |
| Combining Ratio of Parts (Part One:Part Two) | |
| 1:1 | |
| Delivery/Application Method | |
| Hydraulic atomization tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 2.5 min of application to an in vitro tissue model. In vivo models showed relatively faster biodegradation. In vitro models demonstrated significantly lower strength and resilience variability for this example. For the current example, increasing the chitosan content further reduced variability. The formulation is biodegradable and particularly adapted to use as a vascular tissue sealant. In addition due to the limited multidimensional swelling of the example, it is also particularly adapted for use as a dural sealant.

Example 12

| Part One | |
| --- | --- |
| 1. Bovine Serum Albumin | 25.00% |
| 2. Urea | 5.00% |
| 3. Water | 70.00% |
| Part Two | |
| 1. Glutaraldehyde | 4.00% |
| 2. Water | 96.00% |
| Combining Ratio of Parts (Part One:Part Two) | |
| 1:1 | |
| Delivery/Application Method | |
| Hydraulic atomization tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 2 min of application to an in vitro tissue model. In vivo models showed relatively faster biodegradation. The formulation is biodegradable and particularly adapted to use as a vascular tissue sealant. In addition due to the limited multidimensional swelling of the example, it is also particularly adapted for use as a dural sealant.

Example 13

| Part One | |
| --- | --- |
| 1. Bovine Serum Albumin | 25.00% |
| 2. Chitosan | 0.15% |
| 3. Water | 74.85% |
| Part Two | |
| 1. Glutaraldehyde | 4.00% |
| 2. Water | 96.00% |
| Combining Ratio of Parts (Part One:Part Two) | |
| 1:1 | |
| Delivery/Application Method | |
| Hydraulic atomization tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 1.5 min of application to an in vitro tissue model. In vivo models showed relatively faster biodegradation. In vivo models showed relatively faster biodegradation. In vitro models demonstrated significantly lower strength and resilience variability for this example. For the current example, increasing the chitosan content further reduced variability. The formulation is biodegradable and particularly adapted to use as a vascular tissue sealant. In addition due to the limited multidimensional swelling of the example, it is also particularly adapted for use as a dural sealant. Bacteriocidal Testing: The formulation (4:1 dual syringe with auger mixing tip) was placed in a 24-well plate and allowed to cure for 48 hr prior to bacterial challenge with $1 \times 10^5$ cfu/ml of Staph Aureus followed by 6 hr incubation. Samples of uncured formulations were challenged with $1 \times 10^5$ cfu/ml of Staph Aureus followed by 10 min incubation. The present example produced a 3.13 log reduction in bacteria following a 48 hr cure and 6 hr incubation compared to control. Samples of uncured formulations produced a 1.3 log reduction in bacteria following a 10 min incubation compared to control.

Example 14

| Part One | |
| --- | --- |
| 1. Lactoferrin | 35.00% |
| 2. Urea | 5.00% |
| 3. Water | 60.00% |

-continued

| Part Two | |
|---|---|
| 1. Glutaraldehyde | 10.00% |
| 2. Water | 90.00% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 0.5 min of application to an in vitro tissue model. This example delivered in a 1:1 ratio forms a sealant or anti-adhesive mass within 1.5 min of application. The formulations are biodegradable and particularly adapted to use as a vascular tissue sealant. In addition due to the lack of multidimensional swelling of the example, it is also particularly adapted for use as a dural sealant.

Example 15

| Part One | |
|---|---|
| 1. Lactoferrin | 35.00% |
| 2. Urea | 5.00% |
| 3. Chitosan | 0.15% |
| 4. Water | 59.85% |
| Part Two | |
| 1. Glutaraldehyde | 10.00% |
| 2. Water | 90.00% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 0.5 min of application to an in vitro tissue model. This example delivered in a 1:1 ratio forms a sealant or anti-adhesive mass within 2 min of application. In vitro models demonstrated significantly lower strength and resilience variability for this example. For the current example, increasing the chitosan content further reduced variability. The formulations are biodegradable and particularly adapted to use as a vascular tissue sealant. In addition due to the lack of multidimensional swelling of the example, it is also particularly adapted for use as a dural sealant. Bactericidal Testing: The formulation (4:1 dual syringe with auger mixing tip) was placed in a 24-well plate and allowed to cure for 16 hr prior to bacterial challenge with $1\times10^5$ cfu/ml of Staph Aureus followed by 6 hr incubation. Samples of uncured formulations were challenged with $1\times10^5$ cfu/ml of Staph Aureus followed by 10 min incubation. The present example produced a 4.54 log reduction in bacteria following a 16 hr cure and 6 hr incubation compared to control. Samples of uncured formulations produced a 3 log reduction in bacteria following a 10 min incubation compared to control. Swelling Studies: Cylindrical devices of the formulation were produced by dispensing the formulation into a uniform mold and allowing the system to cure for 15 min. Following curing, devices were removed and placed in 0.05 M phosphate buffered saline (pH 7.4) at 37° C. the average changes in weight, length and width for the 4:1 ratio were −11.62%, −4.45%, and 0.41% respectively over a 5 day period of time from the measurements at t=0.

Example 16

| Part One | |
|---|---|
| 1. Lactoferrin | 35.00% |
| 2. Urea | 5.00% |
| 3. Chitosan | 0.15% |
| 4. Water | 59.85% |
| Part Two | |
| 1. Glutaraldehyde | 5.00% |
| 2. Water | 95.00% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 4:1 ratio was evaluated by the inventors for venous and arterial sealant properties. In this ratio the adhesive forms a sealant mass within approximately 0.5 min of application to an in vitro tissue model. This example delivered in a 1:1 ratio forms a sealant or anti-adhesive mass within 1.5 min of application. In vivo models showed relatively faster biodegradation. In vitro models demonstrated significantly lower strength and resilience variability for this example. For the current example, increasing the chitosan content further reduced variability. The formulations are biodegradable and particularly adapted to use as a vascular tissue sealant. In addition due to the lack of multidimensional swelling of the example, it is also particularly adapted for use as a dural sealant.

Example 17

| Part One | |
|---|---|
| 1. Lactoferrin | 35.00% |
| 2. Urea | 5.00% |
| 3. Chitosan | 0.15% |
| 4. Water | 59.85% |
| Part Two | |
| 1. Glutaraldehyde | 4.00% |
| 2. Water | 96.00% |

| Combining Ratio of Parts (Part One:Part Two) |
| --- |
| 1:1 |
| Delivery/Application Method |
| Hydraulic atomization tip |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 1.5 min of application to an in vitro tissue model. In vivo models showed relatively faster biodegradation. In vitro models demonstrated significantly lower strength and resilience variability for this example. For the current example, increasing the chitosan content further reduced variability. The formulation is biodegradable and particularly adapted to use as a vascular tissue sealant. In addition due to the lack of multidimensional swelling of the example, it is also particularly adapted for use as a dural sealant. Swelling Studies: Cylindrical devices of the formulation were produced by dispensing the formulation into a uniform mold and allowing the system to cure for 15 min. Following curing, devices were removed and placed in 0.05 M phosphate buffered saline (pH 7.4) at 37° C. The average change in weight, length and width were −3.6%, −1.3%, and −1.9% respectively over a 5 day period of time from the measurements at t=0.

Example 18

| Part One | |
| --- | --- |
| 1. Lactoferrin | 25.00% |
| 2. Urea | 5.00% |
| 3. Chitosan | 0.15% |
| 4. Glucosamine | 1.00% |
| 5. Water | 68.85% |
| Part Two | |
| 1. Glutaraldehyde | 2.50% |
| 2. Water | 97.50% |
| Combining Ratio of Parts (Part One:Part Two) | |
| 1:1 | |
| Delivery/Application Method | |
| Hydraulic atomization tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 2 min of application to an in vitro tissue model. In vivo models showed relatively faster biodegradation. In vitro models demonstrated significantly lower strength and resilience variability for this example. For the current example, increasing the chitosan content further reduced variability. The formulation is biodegradable and particularly adapted to use as a vascular tissue sealant. In addition due to the lack of multidimensional swelling of the example, it is also particularly adapted for use as a dural sealant.

Example 19

| Part One | |
| --- | --- |
| 1. Lactoferrin | 35.00% |
| 2. Water | 65.00% |
| Part Two | |
| 1. Glutaraldehyde | 10.00% |
| 2. Water | 90.00% |
| Combining Ratio of Parts (Part One:Part Two) | |
| 4:1 & 1:1 | |
| Delivery/Application Method | |
| Dual syringe with auger mixing tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 1.5 min of application to an in vitro tissue model. The formulation is biodegradable and particularly adapted to use as a vascular tissue sealant. In addition due to the lack of multidimensional swelling of the example, it is also particularly adapted for use as a dural sealant.

Example 20

| Part One | |
| --- | --- |
| 1. Lactoferrin | 25.00% |
| 2. Urea | 5.00% |
| 3. Water | 70.00% |
| Part Two | |
| 1. Glutaraldehyde | 4.00% |
| 2. Water | 96.00% |
| Combining Ratio of Parts (Part One:Part Two) | |
| 1:1 | |
| Delivery/Application Method | |
| Hydraulic atomization tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 2 min of application to an in vitro tissue model. In vivo models showed relatively faster biodegradation. The formulation is biodegradable and particularly adapted to use as a vascular tissue sealant. In addition due to the lack of multidimensional swelling of the example, it is also particularly adapted for use as a dural sealant.

Example 21

| Part One | |
|---|---|
| 1. Lactoferrin | 25.00% |
| 2. Chitosan | 0.15% |
| 3. Water | 74.85% |
| Part Two | |
| 1. Glutaraldehyde | 4.00% |
| 2. Water | 96.00% |
| Combining Ratio of Parts (Part One:Part Two) | |
| 1:1 | |
| Delivery/Application Method | |
| Hydraulic atomization tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 2 min of application to an in vitro tissue model. In vivo models showed relatively faster biodegradation. In vitro models demonstrated significantly lower strength and resilience variability for this example. For the current example, increasing the chitosan content further reduced variability. The formulation is biodegradable and particularly adapted to use as a vascular tissue sealant. In addition due to the lack of multidimensional swelling of the example, it is also particularly adapted for use as a dural sealant.

Example 22

| Part One | |
|---|---|
| 1. Lactoferrin | 15.00% |
| 2. Chitosan | 0.15% |
| 3. Water | 84.85% |
| Part Two | |
| 1. Glutaraldehyde | 4.00% |
| 2. Water | 96.00% |
| Combining Ratio of Parts (Part One:Part Two) | |
| 1:1 | |
| Delivery/Application Method | |
| Hydraulic atomization tip | |

The present example possesses characteristics making it operable as a tissue sealant or adhesive. The formulations may be applied to damaged tissues for control of capillary, venous or arterial leakage. This example delivered in a 1:1 ratio was evaluated by the inventors for venous and arterial sealant properties. In this ratio the adhesive forms a sealant or anti-adhesive mass within approximately 2.5 min of application to an in vitro tissue model. In vivo models showed relatively faster biodegradation. In vitro models demonstrated significantly lower strength and resilience variability for this example. The formulation is biodegradable and particularly adapted to use as a vascular tissue sealant. In addition due to the lack of multidimensional swelling of the example, it is also particularly adapted for use as a dural sealant. Swelling Studies: Cylindrical devices of the formulation were produced by dispensing the formulation into a uniform mold and allowing the system to cure for 15 min. Following curing, devices were removed and placed in 0.05 M phosphate buffered saline (pH 7.4) at 37° C. the average change in weight, length and width were 10.4%, 4.2%, and 6.2% over a 5 day period of time from the measurements at t=0.

We claim:

1. A composition having first and second parts, which upon combination is useful as a tissue sealant, tissue dressing, tissue barrier, or tissue adhesive comprising: (a) an amino acid containing compound or composition selected from the group consisting of lactoferrin, lactoferrin peptides, lactoferrin hydrolysates, derivatives of this group, and any combination thereof in the first part; (b) an aldehyde or polyaldehyde in the second part; and the first and the second parts are separate parts of the composition prior to combination.

2. The composition of claim 1 further comprising at least one compound selected from the group consisting of urea, chitosan, glucosamine, and dextran in the first part.

3. A method of producing a tissue dressing for application at a desired site of a subject, the method comprising reacting an effective amount of the composition of claim 1 by mixing to produce a crosslinked and solidified tissue dressing.

4. A composition useful as a tissue dressing, which is produced by the method of claim 3.

5. A method for effectively sealing, coating and adhering a tissue at a desired site of a subject, the method comprising administering by positive pressure an effective amount of the composition of claim 1, at the site for a period of time effective to seal, coat, or adhere the tissue at the site by crosslinking the composition at least in part with tissue proteins at the desired site.

6. A method for effectively sealing, coating and adhering a tissue at a desired site of a subject, the method comprising administering by positive pressure an effective amount of the composition of claim 2, at the site for a period of time effective to seal, coat, or adhere the tissue at the site by crosslinking the composition at least in part with tissue proteins at the desired site.

7. A method of using the tissue dressing of claim 4, the method comprising applying the tissue dressing at a desired site of a subject.

8. A system comprising at least independent first and second syringes, which are joined by a union tip, and the composition of claim 1; wherein the first part of the composition is contained in the first syringe, the second part of the composition is contained in the second syringe, and the first and the second parts are combined at the union tip.

9. A system comprising at least independent first and second syringes, which are joined by a union tip, and the composition of claim 2; wherein the first part of the composition is contained in the first syringe, the second part of the composition is contained in the second syringe, and the first and the second parts are combined at the union tip.

* * * * *

UNITED STATES PATENT AND TRADEMARK OFFICE
CERTIFICATE OF CORRECTION

PATENT NO.        : 8,673,335 B2                                                    Page 1 of 1
APPLICATION NO. : 12/441224
DATED             : March 18, 2014
INVENTOR(S)       : Jones et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 390 days.

Signed and Sealed this
Twenty-ninth Day of September, 2015

Michelle K. Lee
*Director of the United States Patent and Trademark Office*